US007785463B2

(12) United States Patent
Bissler et al.

(10) Patent No.: US 7,785,463 B2
(45) Date of Patent: Aug. 31, 2010

(54) EXTRACORPOREAL RENAL REPLACEMENT MODELING SYSTEM

(75) Inventors: John J. Bissler, Cincinnati, OH (US); Nat Hemasilpin, Cincinnati, OH (US); Marios M. Polycarpou, Strovolos (CY)

(73) Assignee: Children's Hospital Medical Center, Cincinnati, OH (US)

( * ) Notice: Subject to any disclaimer, the term of this patent is extended or adjusted under 35 U.S.C. 154(b) by 1069 days.

(21) Appl. No.: 11/378,051

(22) Filed: Mar. 17, 2006

(65) Prior Publication Data
US 2007/0215545 A1 Sep. 20, 2007

(51) Int. Cl.
*B01D 61/32* (2006.01)
*B01D 61/22* (2006.01)
*A61M 1/14* (2006.01)

(52) U.S. Cl. .................. 210/143; 210/85; 210/87; 210/96.2; 210/97; 210/103; 210/134; 210/141; 210/252; 210/258; 210/259; 210/321.65; 604/4.01; 604/6.09; 604/6.11; 604/65; 604/66; 604/67

(58) Field of Classification Search ............... 210/85, 210/87, 96.2, 97, 103, 134, 141, 143, 252, 210/258, 259, 321.65, 646; 604/4.01, 5.04, 604/6.09, 6.11, 65, 66, 67
See application file for complete search history.

(56) References Cited

U.S. PATENT DOCUMENTS

| | | | |
|---|---|---|---|
| 4,324,663 | A | 4/1982 | Hirel et al. |
| 5,211,849 | A | 5/1993 | Kitaevich et al. |
| 5,344,568 | A | 9/1994 | Kitaevich et al. |
| 5,938,938 | A | 8/1999 | Bosetto et al. |
| 6,200,485 | B1 | 3/2001 | Kitaevich et al. |
| 6,471,872 | B2 | 10/2002 | Kitaevich et al. |
| 6,780,322 | B1 | 8/2004 | Bissler et al. |
| 2002/0055672 | A1 | 5/2002 | Zhang |
| 2003/0006175 | A1* | 1/2003 | Kawaguchi ............... 210/87 |
| 2004/0168988 | A1* | 9/2004 | Ikeda ..................... 210/744 |

FOREIGN PATENT DOCUMENTS

DE 19821534 C1 8/1999

(Continued)

OTHER PUBLICATIONS

European Patent Office, International Search Report issued in corresponding PCT Application serial No. PCT/US2007/064169 dated Aug. 28, 2007 (5 pages).

(Continued)

*Primary Examiner*—John Kim
(74) *Attorney, Agent, or Firm*—Wood, Herron & Evans LLP

(57) ABSTRACT

A system, program product and method continuously optimize an ultrafiltration rate during an extracorporeal renal replacement process by modeling physiological and actual rate data. The system maps the sensed, physiological data to a mathematical model to assess the data in terms of the ultrafiltration rate. The model provides parameters used to predict where the treatment is headed based on current conditions. The system processes the parameters in terms of preset criteria to generate the optimized ultrafiltration rate. Where the system is networked, communication of the data may be accomplished using remote and online communication techniques.

10 Claims, 4 Drawing Sheets

FOREIGN PATENT DOCUMENTS

| | | |
|---|---|---|
| EP | 1275407 A1 | 1/2003 |
| WO | 0066197 A1 | 11/2000 |
| WO | 0108723 A1 | 2/2001 |

OTHER PUBLICATIONS

Schreiber, Martin J., Jr., M.D., Clinical Dilemmas in Dialysis: Managing the Hypotensive Patent, Setting the Stage, American Journal of Kidney Diseases, vol. 38, No. 4, Oct. 2001 (12 pages).

Daugirdas, John T., M.D., Clinical Dilemmas in Dialysis: Managing the Hypotensive Patient, Pathophysiology of dialysis hypotension: An Update, American Journal of Kidney Diseases, vol. 38, No. 4, Oct. 2001 (9 pages).

John, S. Anitha, BS, PH.D., et al., Nonocclusive Mesenteric Infarction in Hemodialysis Patients, J. Am. Coll. Surg., vol. 190, pp. 84-88, 2000.

Misra, Madhukar et al., Effect of Cause and Time of Dropout on the Residual GFR: A Comparative Analysis of the Decline of GFR on Dialysis, Kidney Int., vol. 59, pp. 754-763, 2001.

Canada-USA (CANUSA), Peritoneal Dialysis Study Group, Adequacy of Dialysis and Nutrition in Continuous Peritoneal Dialysis: Association with Clinical Outcomes, J Am Soc Nephrol, vol. 7, pp. 198-207, 1996.

Sherman, Richard A., MD, Clinical Dilemmas in Dialysis: Managing the Hypotensive Patient, Modifying the Dialysis Prescription to Reduce Intradialytic Hypotension, American Journal of Kidney Diseases, vol. 38, No. 4, Oct. 2001 (11 pages).

Schlaeper, Christian, et al., High Clearance Continuous Renal Replacement Therapy With A Modified Dialysis Machine, Kidney International, vol. 56, Suppl. 72 (1999), pp. 8-20-8-23.

Van Kuijk, Willy H.M., et al., Critical Role of the Extracorporeal Blood Temperature in the Hemodynamic Response During Hemofiltration, Journal of the American Society of Nephrology, vol. 8, pp. 949-955, 1997.

Maggiore, Q., et al., Cardiovascular Stability During Haemodialysis, Haemofiltration and Haemodiafiltration, Nephrol Dial Transplant (2000) 15 [Suppl 1], pp. 68-73, 2000.

Van Der Sande, Frank M. et al., Energy Transfer is the Single Most Important Factor for the Difference in Vascular Response between Isolated Ultrafiltration and Hemodialysis, J Am Soc Nephrol, vol. 11, pp. 1512-1517, 2000.

Van Der Sande, Frank M., et al., Effect of Intravenous Fluids on Blood Pressure Course during Hemodialysis in Hypotensive-Prone Patients, J Am Soc Nephrol, vol. 11, pp. 550-555, 2000.

Meers, Carol et al., Reducing Complications During Demodialysis Using Gradient Ultrafiltration with Gradient Sodium Dialysate, ANNA Journal, Oct. 1999, vol. 26, No. 5, pp. 495-505, 1999.

Petitclerc, T., et al., Dialysis Sodium Concentration: What is Optimal and Can it be Individualized?, Nephrol Dial Transplant, vol. 10, No. 5, pp. 596-599, 1995.

Koomans, Hendrik A., et al., Plasma Volume Recovery after Ultrafiltration in Patients with Chronic Renal Failure, Kidney International, vol. 26, (1984), pp. 848-854.

Schneditz, Daniel, et al., A Blood Protein Monitor for the Continuous Measurement of Blood Volume Changes During Hemodialysis, Kidney International, vol. 38 (1990), pp. 342-346.

Leypoldt, John K., et al., Determination of Circulating Blood Volume by Continuously Monitioring Hematocrit During Hemodialysis, Journal of the American Society of Nephrology, vol. 6, No. 2, 214-219 (1995).

Johner, Christian, et al., Evaluation of an Ultrasonic Blood Volume Monitor, Nephrol Dial Transplant, (1998), vol. 13, pp. 2098-2103.

Krepel, Harmen P., et al., Variability of Relative Blood Volume During Haemodialysis, Nephrol Dial Transplant (2000) vol. 15, pp. 673-679.

Coli, Luigi, et al., A Simple Mathematical Model Applied to Selection of the Sodium Profile During Profiled Haemodialysis, Nephrol Dial Transplant, (1998), vol. 13, pp. 404-416.

Perazella, Mark A., M.D., FACP, Clinical Dilemmas in Dialysis: Managing the Hypotensive Patient, Pharmacologic Options Available to Treat Symptomatic Intradialytic Hypotension, American Journal of Kidney Diseases, vol. 38, No. 4, Oct. 2001 (12 pages).

Guyton, Arthur C., Textbook of Medical Physiology, Sixth Edition, W.B. Saunders Company, Philadelphia, London, Toronto, Chapter 31, pp. 370-382, 1981.

Grodins, Fred S., Integrative Cardiovascular Physiology: A Mathematical Synthesis of Cardiac and Blood Vessel Hemodynamics, Quarterly Review of Biology, vol. 34, No. 2, Jun. 1959, pp. 93-116.

Wiederhielm, Curt A., Dynamics of Transcapillary Fluid Exchange, J. Gen. Physiol., vol. 52, p. S29, 1968.

Kimura, Genjiro, et al., A Simulation Study on Transcellular Fluid Shifts Induced by Hemodialysis, Kidney International, vol. 24 (1983), pp. 542-548.

Hypertension Diagnostics, Inc., HDI/PulseWave CR-2000, Product Brochure, 2000 (2 pages).

Respironics, NICO Cardiopulmonary Management System, Product Brochure, http://nico.respironics.com, undated (5 pages).

HEMA Metrics, Criti-Line III, Product Description, www.hemametrics.com, undated (1 page).

* cited by examiner

EXTRACORPOREAL RENAL REPLACEMENT MODELING SYSTEM

FIELD OF THE INVENTION

The present invention generally relates to systems and methods of extracorporeal renal replacement therapy and, more particularly, to control systems and methods for operating a pump in an extracorporeal renal replacement system.

BACKGROUND OF THE INVENTION

Several extracorporeal renal replacement procedures, such as dialysis, hemodialysis, hemofiltration, hemodiafiltration, ultrafiltration, and plasmapheresis are used to provide replacement or supplementation of a patient's natural renal function in order to remove fluid and/or waste products from their blood. The specific procedure is tailored to the specific needs of the particular patient. For example, dialysis is used to remove soluble waste and solvent from blood. Hemofiltration is used to remove plasma water and dissolved waste from blood while replacing the removed volume with replacement solution. Hemodiafiltration is used to remove both unwanted solute (soluble waste) and plasma water from blood. Ultrafiltration is a species of hemofiltration where only volume and dissolved components are released; and plasmapheresis is used to remove blood plasma by means of a plasmapheresis filter.

For certain patients, renal replacement procedures may extend over hours, days, months and even years. In general, current systems for monitoring and controlling renal replacement procedures lack the flexibility and accuracy required to perform such procedures on neonates. This is mainly due to the absence of a satisfactory automatic control of the pumps employed. Because of the patient risk involved in using such equipment, health care personnel may measure the fluid removed from the patient on an hourly basis. The continuing need to monitor the fluid removed and patient responses lead to a significant increase in nursing care and, thus, increases the cost of the therapy. Therefore, there is a need to improve the level of autonomy for the systems such that the procedure is less time consuming for medical personnel, and consequently less costly. However, the enhanced autonomy must not come at the expense of patient safety.

Due to the time-varying nature of renal function replacement and supplementation systems, the dynamics of fluid pumping may change over time. For example, the characteristics of system components such as tubing, filter, and connectors may vary slowly over time due to protein deposit or as occlusion of the path for fluid flow. As the membrane changes, the pumping rate of the pump must be altered to compensate for the altered filter to maintain the same function. Current systems for monitoring and controlling renal replacement procedures lack the ability to autonomously correct these time-dependent flow rate variations with high accuracy, rapid response, and minimal overshoot or transient variations following correction. In one sense, most conventional systems, at best, tend to be reactive, rather than proactive, during a procedure.

A particular need for the ability to control fluid pumping arises in patients undergoing hemodialysis. During a hemodialysis procedure, dissolved materials are removed from the blood and added to the blood down their respective concentration gradients. In addition, plasma water and dissolved content are removed through a porous membrane down a pressure gradient in a process known as ultrafiltration. The clinical problem observed during hemodialysis is that, during the intrinsic dual treatment processes, replacement of renal function reduces the patient's intravascular or blood volume. This impacts the heart's ability to pump blood to the tissues and causes many unwanted side effects including, but not limited to, cramping, nausea, vomiting, and diaphoresis. Such cardiac function compromises can also challenge blood flow to the heart itself and cause arrhythmia or even a heart attack.

Conventional solutions to these adverse side effects is to buffer the intravascular volume reduction with effecting a change in the osmotic fluid shift. While some patients may respond, the effects are not very often consistent and, in particular, patients with intradialytic hypotension (IDH) continue to have problems. The consequences of IDH may include pain, loss of functional days and death.

Another conventional approach is to monitor the patient's hematocrit on line and use the hematocrit measurements to monitor the blood volume. The deficiency of this conventional approach is that, if one makes an adjustment based on the hematocrit, the system changes as the fluid removal rate also alters the cardiovascular physiology. Consequently, the target for alleviating the heart's inability to pump blood to the tissues will continuously shift without control. Merely reducing the fluid removal rate may paradoxially induce a state that could worsen the hypotension by interfering with the bodies physiologic response.

Therefore, there is a need for an improved hemodialysis system that can overcome these and other deficiencies of conventional hemodialysis systems.

SUMMARY OF THE INVENTION

According to the principles of the present invention and in accordance with the described embodiments, one aspect of the invention provides a system, program product and method for optimizing an ultrafiltration rate during a blood filtration process. The ultrafiltration rate may be optimized by modeling physiological and actual flow rate data. The system maps the sensed, physiological data to a mathematical model to assess the data in terms of the ultrafiltration rate. The model provides model parameters used to predict where the treatment is headed based on current conditions. The system may process the parameters in terms of preset criteria to generate the optimized ultrafiltration rate.

Embodiments of the invention more particularly include an extracorporeal renal replacement system for fluid removal from the blood of a patient. The system includes pumps for pumping liquid such as dialysate or infusate, drained fluid, and blood in the hemofiltration system. A flow rate sensor measures the flow rate of fluid in the system generated by the pump and provides flow rate data signals to a controller. Patient sensor, measures physiological conditions of the patient and generates patient sensor data signals that are also communicated to the controller. The controller communicates with the pump and analyzes the flow rate data signals and the patient parameter data signals using the model. The controller then initiates generation an output signal for the pump to adjust the flow rate of the liquid. The adjustment may be continuously and dynamically accomplished, and the communication with the controller may be networked and/or wireless.

Processes of the invention may include receiving and using a model to process flow rate data and physiological condition to determine a model parameter. The model parameter may be used to generate an output signal configured to adjust the flow rate realized by a pump. The model parameter may be compared or otherwise processed in conjunction with criteria to determine if the ultrafiltration rate can be optimized. For instance, if the model parameter fails to conform with the criteria, then the ultrafiltration rate may be reduced. If the model parameter alternatively conforms with the criterion, then the ultrafiltration rate may be increased or otherwise further optimized.

Features of the invention also include program code configured to cause the controller to receive flow rate and physiological condition data. The program code executed by the controller uses the model to process the flow rate data and the physiological condition data to determine a model parameter, which is used to generate an output signal configured to adjust the flow rate realized by a pump. A signal bearing medium bears the program code.

Ultrafiltration may be accomplished in manner that mitigates the problems of the prior art. The system is proactive in nature, rather then merely reactive, anticipating and correcting potential problems before they occur. Moreover, the system and method of the invention are advantageous because of the multipurpose nature thereof, the repeatability and accuracy of the processes, and the simultaneous, continuous flow of fluids in an extracorporeal blood circuit, while being equally applicable to adult, pediatric and neonatal patients.

Implementation of either or both of the aforementioned adaptive or supervisory control may increase the autonomy of an extracorporeal renal replacement system. Various advantages follow from the enhanced autonomy. For example, the continuous monitoring and control reduces medical costs and improves the quality of medical care by reducing the need for intermittent supervision of the extracorporeal renal replacement procedure by clinical staff.

These and other benefits and advantages of the present invention will become more readily apparent during the following detailed description taken in conjunction with the drawings herein.

DETAILED DESCRIPTION OF THE INVENTION

Figure 1:
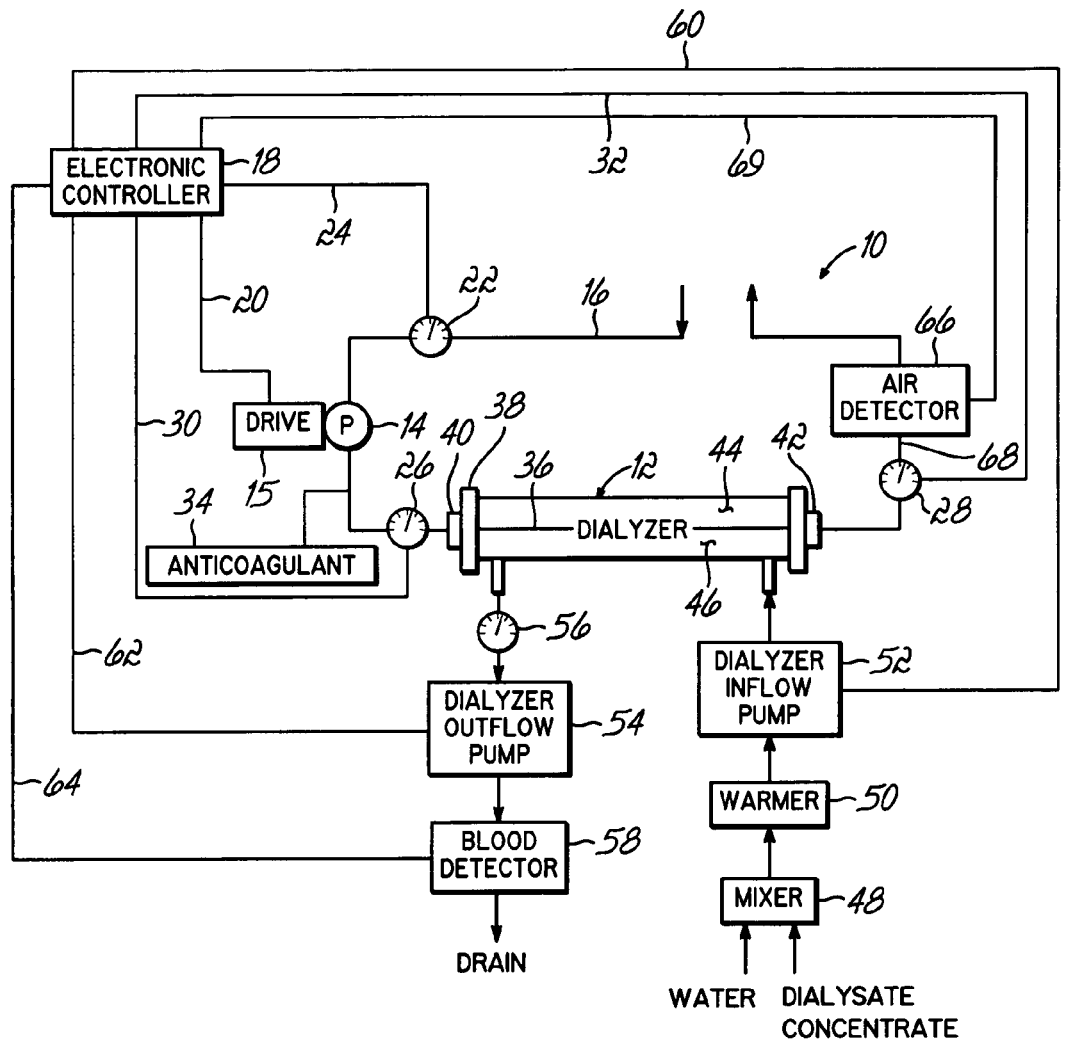
FIG. 1 is a schematic representation of an extracorporeal renal replacement system configured to optimize an ultrafiltration rate used during a blood filtration process.

FIG. 1 shows a system 10 configured to continuously optimize an ultrafiltration rate during a filtration process by modeling physiological and actual rate data. The system 10 maps the sensed, physiological data to a mathematical model to assess the data in terms of the ultrafiltration rate. The model provides parameters used to predict where the treatment is headed based on current conditions. The system 10 may process the parameters in terms of preset criteria to generate the optimized ultrafiltration rate.

Turning more particularly to FIG. 1, a extracorporeal renal replacement system 10 generally includes an extracorporeal hydraulic circuit with a filter, such as a filter 12 and a blood flow pump 14 that directs a flow of blood to be cleaned from the circulatory system of a patient (not shown), which may be an adult, pediatric or neonatal patient, to the filter 12. An arterial blood line defined by convention in the form of an inlet conduit 16 is connected with the patient with a suitable catheter (not shown) providing an access site to an artery of the patient's cardiovascular system or to a port on a catheter. The inlet conduit 16 includes an internal lumen through which blood is pumped by the blood flow pump 14.

Blood flow pump 14 withdraws blood from the patient by a pumping action that causes blood to flow from the access site through the inlet conduit 16 toward the filter 12 and establishes a continuous flow during system operation to the filter 12. The blood flow rate established in the inlet conduit 16 may range from about 30 ml/min to about 700 ml/min. Blood flow pump 14 may be of the roller or peristaltic type that comprises a track for receiving a section of the inlet conduit 16 and a rotor that intermittently applies pressure to this section to cause flow. Blood flow pump 14 has a drive unit 15 that is electrically coupled with controller 18 over a communication link 20, such as a wire, radiofrequency (RF) link, or infrared (IR) link.

Upstream from the blood flow pump 14 is a pressure transducer 22 that is electrically coupled with controller 18 over a communication link 24, such as a wire, radiofrequency (RF) link, or infrared (IR) link. The pressure transducer 22 monitors the arterial pressure, which typically represents the negative pressure created by the suction of blood flow pump 14, by sensing the fluid pressure inside the conduit 16 at a location in the hydraulic circuit between the patient and the blood flow pump 14.

Upstream and downstream from the filter 12 are a pair of pressure transducers 26, 28. Pressure transducer 26 senses the venous fluid pressure of the blood stream flowing in inlet conduit 16 downstream from the blood flow pump 14 and upstream from the filter 12. Similarly, pressure transducer 28 senses the arterial fluid pressure of the blood stream flowing in inlet conduit 16 downstream from the filter 12. The pressure transducers 26, 28 may communicate pressure measurements to the controller 18 over respective communication links 30, 32, such as a wire, RF link, or IR link.

The controller 18 may use the downstream and upstream pressure indications received from the pressure transducers 26, 28 to determine a pressure drop across the filter 12 from the pressure differential. The pressure drop arises from the flow restriction represented by the filter 12 and increases as the filter 12 ages with use. If the pressure drop reaches a set upper level, this may indicate that the filter 12 needs regeneration or replacement. The pressure transducers 26, 28 may each be any conventional type of pressure sensing device capable of sensing or measuring fluid pressure, generating an analog or digital signal indicating the sensed fluid pressure, and communicating an indication of the fluid pressure as a digital or analog electrical signal to the controller 18. Pressure transducers 26, 28 may be configured to measure either total pressure or static pressure, and may be any one of numerous pressure sensing devices known in the art including, but not limited to, a capacitance sensor, a strain gauge sensor, a piezoresistive sensor, and a thermal sensor. Drip chambers (not shown) may also be used to facilitate the pressure measurements.

Upstream from the filter 12 is a medicament source 34 that permits the injection or infusion of desired fluids, including drugs, medications, and anticoagulants such as heparin or citrate into the stream of the patient's blood being pumped through the inlet conduit 16. The injection or infusion of such medicament fluids to the blood stream flowing in inlet conduit 16 may be accomplished in any conventional manner as understood by a person having ordinary skill in the art and maybe quite close to the arterial inlet.

The filter 12 includes a semi-permeable membrane 36 that is housed within a container 38 having an inlet 40 coupled hydraulically with the inlet conduit 16 and an outlet 42. The membrane 36, which may have the form of a large number of semi-permeable hollow fiber membranes, divides the container 38 into a blood compartment 44 and a dialysate compartment 46. When the system 10 is operating, a continuous blood stream is directed from the inlet 40 into blood compartment 44 on one side of the membrane 36 and, simultaneously, a continuous dialysate stream is supplied to dialysate compartment 46 on the opposite side of the membrane 36.

The filter 12 removes toxic substances normally eliminated in a healthy patient's urine from the stream of blood by a diffusion mechanism established by a concentration gradient across the membrane 36 created by the flowing blood and dialysate. Substances containing plasma water are also filtered by a pressure gradient established across the semi-permeable membrane 36 from the blood stream flowing in blood compartment 44 to the dialysate flowing in dialysate compartment 46. The dialysate, which is typically a water-based solution, absorbs the substances transported through the membrane 36 and removes those substances as a component of a spent dialysate stream for subsequent disposal.

A mixer 48 generates a continuous supply of dialysate for use in the filter 12 by combining and blending a dialysate concentrate with water. A warmer 50 receives an output stream of dialysate from the mixer 48 and elevates the temperature of the fresh dialysate supplied to compartment 46 to near body temperature. The dialysate is moved through the filter 12 using a dialysate inflow pump 52 located on an inlet side of the filter 12 and a dialysate outflow pump 54 located on an output side of the filter 12. These pumps 52, 54, which have adjustable flow rates, regulate the pressure of the dialysate, as monitored by a pressure transducer 56 on the dialysate outflow from dialysate compartment 46. A blood detector 58 monitors for the presence of blood as a contaminant in the spent dialysate, which is routed to a sanitary drain for disposal. The pumps 52, 54 and blood detector 58 are coupled electrically with the controller 18 by respective communications links 60, 62, 64.

The outlet 42 from the blood compartment 44 of the filter 12 is coupled hydraulically with a venous bloodline or outlet conduit 68. The outlet conduit 68 is connected with the circulatory system of the patient with a suitable catheter (not shown) providing an access site to a vein of the patient's cardiovascular system. The outlet conduit 68 includes an internal lumen through which cleaned or dialyzed blood is pumped by the blood flow pump 14 and returned to the patient's circulatory system.

An air detector 66 communicates with the outlet conduit 68 to check for the presence of air bubbles or foam in the flow of dialyzed blood. Air detector 66, which is located downstream from the filter 12 and which may be any conventional air detector suitable for this purpose, is coupled electrically with the controller 18 by a communications link 69.

Typically, the inlet and outlet conduits 16, 68 are transparent or translucent such that the stream of blood at any given time is visible for perceiving irregularities in flow. For example, the inlet and outlet conduits 16, 68 may be made of flexible polyvinylchloride tubing.

The controller 18 exercises supervisory control over the operation of the system 10. The controller 18 may be a programmable logic controller ("PLC") or another microprocessor-based controller capable of executing software and carrying out the functions described herein, as is described below in greater detail. The controller 18 includes a suitable user interface (not shown), such as a touch screen display, an alphanumeric keyboard and/or a pointing device, capable of accepting commands or input from the operator and transmitting the input to the data processing unit of controller 18. The controller 18 may display information, such as the current operating status of the system 10 and includes a video display. The controller 18 may further include push buttons to manually initiate or halt certain machine functions and one or more alarms or indicators that warn the operator of the existence of an alarm condition, such as abnormal operation or component failure, in the system 10. The controller 18 communicates with the various sensors of the system 10 and controls the operation of the pumps in the system 10.

Figure 2:
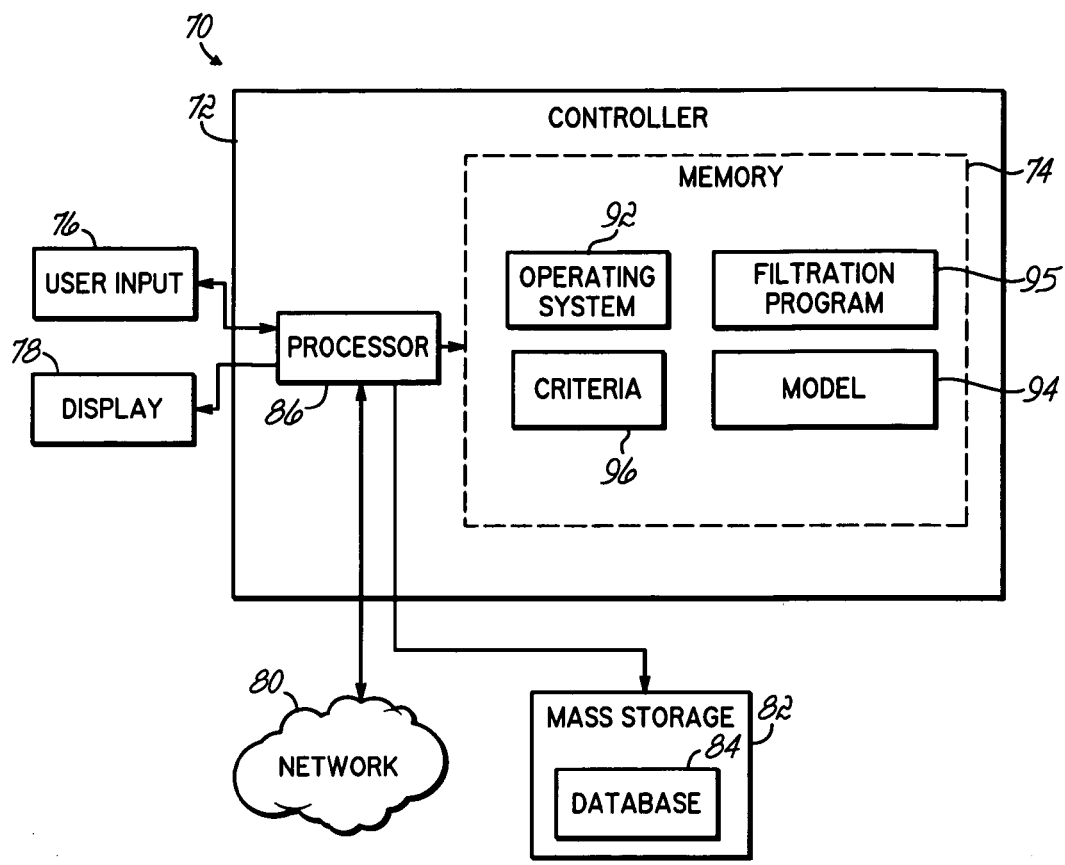
FIG. 2 is a schematic representation of a controller configured for use within the system of FIG. 1.

FIG. 2 shows a block diagram of a controller such that may be used in connection with the system of FIG. 1. The controller of FIG. 2 more particularly comprises a networked computer system 70 having one or more client computer(s) 72 coupled to a network 80. Network 80 represents a networked interconnection, including, but not limited to local-area, wide-area, wireless, and public networks (e.g., the Internet). Moreover, any number of computers and other devices may be networked through network 80, e.g., multiple servers (not shown). Computer system 70 will hereinafter also be referred to as a "controller," "apparatus," "microchip," "computer," or "processing system," although it should be appreciated that the terms may respectively include many other controller configurations. Moreover, while only one computer 72 is shown in FIG. 1, any number of computers and other devices may be networked through network 80. In still another embodiment, the system could be implemented in a stand-alone configuration, i.e., disconnected from another computer or computer network. Moreover, applicable connections between components of the system 70 may be wireless, where desired.

Computer 72 typically includes at least one processor 86 coupled to a memory 74. Processor 86 may represent one or more processors (e.g., microprocessors), and memory 74 may represent the random access memory (RAM) devices comprising the main storage of computer 72, as well as any supplemental levels of memory, e.g., cache memories, non-volatile or backup memories (e.g., programmable or flash memories), read-only memories, etc. In addition, memory 74 may be considered to include memory storage physically located elsewhere in computer 72, e.g., any cache memory present in processor 86, as well as any storage capacity used as a virtual memory, e.g., as stored within a database 84, or on another computer coupled to computer 72 via network 80.

Computer 72 also may receive a number of inputs and outputs for communicating information externally. For interface with a user, computer 72 typically includes one or more input devices 76 (e.g., a keyboard, a mouse, a trackball, a joystick, a touch pad, iris/fingerprint scanner, and/or a microphone, among others).

The computer 72 additionally includes a display 78 (e.g., a CRT monitor, an LCD display panel, and/or a speaker, among others). It should be appreciated, however, that with some implementations of the computer 72, direct user input and output may not be supported by the computer, and interface with the computer may be implemented through a computer or workstation networked with the computer 72.

For additional storage, computer 72 may also include one or more mass storage devices 82 configured to store, for instance, a database 84. Exemplary devices 82 can include: a floppy or other removable disk drive, a flash drive, a hard disk drive, a direct access storage device (DASD), an optical drive (e.g., a CD drive, a DVD drive, etc.), and/or a tape drive, among others. Furthermore, computer 72 may include an interface with one or more networks (e.g., a LAN, a WAN, a wireless network, and/or the Internet, among others) to permit the communication of information with other computers coupled to the network 80. It should be appreciated that computer 72 typically includes suitable analog and/or digital interfaces between processor 86 and each of components 74, 76, 82, 78 and 80.

Computer 72 operates under the control of an operating system 92, and executes various computer software applications, components, programs, modules, e.g., a model and associated program 94, a filtration program 95 and stored criteria 96, among others. A model for purposes of this specification may include a theoretical construct that represents a physical or biological process, with a set of variables and a set of logical and quantitative relationships between them. Embodiments of the present invention use a mathematical model, which includes mathematical language to describe the behavior of a system. For instance, the system 70 is configured to use a mathematical model comprising a series of mathematical equations descriptive of hemodynamic parameters.

Various applications, components, programs, markers, modules, etc. may also execute on one or more processors in another computer coupled to computer 72 via a network 80, e.g., in a distributed or client-server computing environment, whereby the processing required to implement the functions of a computer program may be allocated to multiple computers over a network.

The memory 74 shown in FIG. 2 includes various data components that may be utilized by the programs to accomplish a system design. As with other memory components described herein, the data may be stored locally as shown in FIG. 2, or may alternatively be remotely accessed. Examples of such data include equations comprising the model, as well as cached model parameters.

Though not shown in FIG. 1, one skilled in the art will appreciate that a server computer may include many of the same or similar components as included in the computer 72, where a networked design processes implementation is desired. In such a situation, for example, the server computer may be remote, e.g., at a nurses' station, while computer 72 may be proximate the pump 52.

The discussion hereinafter will focus on the specific routines utilized to automatically design dispensing systems. In general, the routines executed to implement the embodiments of the invention, whether implemented as part of an operating system or a specific application, component, program, marker, module or sequence of instructions will be referred to herein as "programs," or simply "program code." The programs typically comprise one or more instructions that are resident at various times in various control device memory and storage devices. When a program is read and executed by a processor, the program causes the access control device to execute steps or elements embodying the various aspects of the invention.

Moreover, while the invention has and hereinafter will be described in the context of fully functioning access control devices, such as computer systems, those skilled in the art will appreciate that the various embodiments of the invention are capable of being distributed as a program product in a variety of forms, and that the invention applies equally regardless of the particular type of computer readable signal bearing media used to actually carry out the distribution. Examples of computer readable signal bearing media include but are not limited to recordable type media such as volatile and non-volatile memory devices, floppy and other removable disks, hard disk drives, optical disks (e.g., CD-ROM's, DVD's, etc.), among others, and transmission type media such as digital and analog communication links.

In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 3:
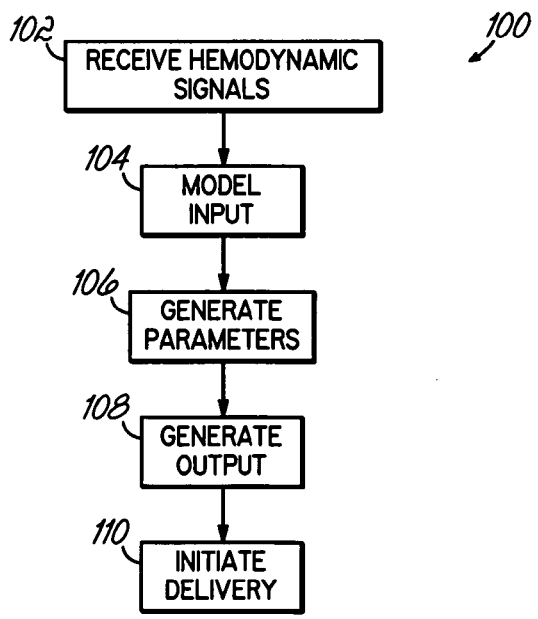
FIG. 3 is a flowchart having steps executable by the controller of FIG. 2 for conducting the blood filtration process.

FIG. 3 shows a flowchart 100 having a sequence of steps for automatically determining an ultrafiltration rate. The flowchart 100 more particularly shows processes that may be executed by the controllers 18 and/or 70 of FIGS. 1 and 2, respectively, to continuously optimize the ultrafiltration rate.

At block 102 of FIG. 3, the controller 70 receives hemodynamic input signals. The hemodynamic input signals include patient driven, physiological data received from one or more sensors, and/or input from the system, such as from the transducers 26, 28 of FIG. 1. Exemplary hemodynamic input signals may convey physiological data indicative of blood pressure, heart rate, arterial pressure, a temperature differential, and hematocrit, for instance. Where the system 10 is networked, such monitoring may be accomplished using remote and online communication and monitoring techniques.

These input signals are processed using the hemodynamic model at block 104, along with any current ultrafiltration rate data. That is, the controller 70 maps the physiological data from the input signals to a series of equations comprising the model 94 to assess the physiological data of the patient in terms of the ultrafiltration rate. The model 94, in a sense, provides a perspective on where the treatment is headed based on current conditions. The controller 70 then initiates at block 106 generation of the ultrafiltration rate that will achieve the desired output at block 110, and the processes continuously repeats. That is, the controller 70 will then generate at block 108 output signals configured to realize the desired ultrafiltration rate, which is delivered to the patient at block 110 of FIG. 3.

Figure 4:
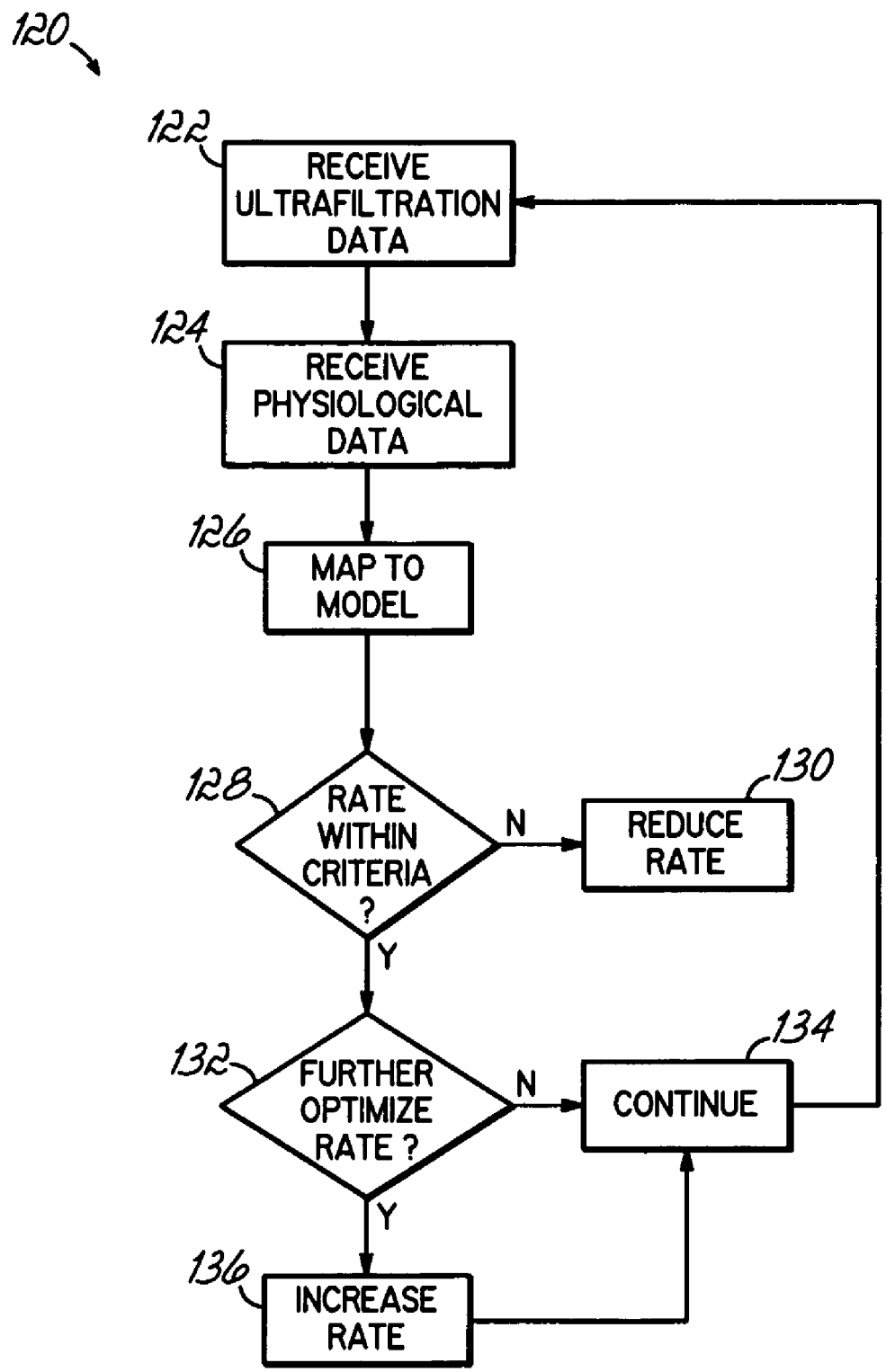
FIG. 4 is a flowchart having steps executable by the controller of FIG. 2 for optimizing the ultrafiltration rate used during the blood filtration process.

FIG. 4 shows a flowchart 120 having steps suited to optimize the control signals driving the ultrafiltration rate. As such, the processes of the flowchart 120 may have application in the context of block 106 of FIG. 3. At block 122 of FIG. 4, the controller 70 may receive flow rate, or ultrafiltration rate data, i.e., the speed at which the pump 52 delivers the infusate or dialysate, in addition to hematocrit readings.

In addition to the ultrafiltration rate data, the controller 70 may receive patient physiological condition data at block 124. As discussed herein, such data may include a patient's heart rate, blood pressure, heart rate, plasma return rate and changes associated therewith. This physiological data may be monitored locally or remotely, i.e., online via a computer network, and generally indicates how a patient is handling the extracorporeal renal replacement process. To this end, a more comprehensive (though non-exhaustive) list of physiological data may be monitored online includes: systemic arterial pressure, pulse pressure, pulse rate, estimated cardiac ejection fraction, estimated stroke volume, estimate stroke volume index, estimated cardiac output, estimated cardiac index, large artery elasticity index (capacitive arterial compliance), small artery elasticity index, systemic vascular resistance, and total vascular impedance.

The ultrafiltration data and physiological data inputs are mapped to the mathematical model 94 at block 126 of FIG. 4. The mathematical model 94 includes equations and calculations used to generate data indicative of a predicted status for parameters. The results of the model analysis, i.e., the model parameters, are then used at block 128 to determine if the modeled results are within a predetermined ultrafiltration rate criteria 96. For instance, the controller 70 at block 128 may determine if the modeled parameters determined at block 126 are within a window or range of values associated with an accepted, predetermined ultrafiltration rate. This criteria 96 may be input as a function of the size and cardiovascular state of a patient, for instance. The criteria 96, in one sense, acts as a comparator against which the modeled parameters are evaluated. The criteria 96 comprises safe bounds in which modeled parameter should reside during a successful ultrafiltration procedure. In one sense, features of the invention determine at block 128 whether the predicted model parameters are within a body's ability to respond to changes.

If the controller 70 determines at block 128 that the ultrafiltration rate is not within acceptable limits, then the ultrafiltration rate may be too fast. As such, the controller 70 may reduce the ultrafiltration rate at block 130 in accordance with the modeled results. For instance, the controller may determine that the ultra-filtration rate excess line and will overwhelm the normal physiological response. In response, the controller 70 may access a lookup table or algorithm used to determine by what percentage the ultrafiltration rate should be reduced in order to bring the parameter within the acceptable limit. A modeled comparison may involve one or more parameters, and a resultant ultrafiltration rate determination typically accounts for the multiple parameters. For example, the physiologic data may reveal an increasing hematocrit outside of acceptable criteria, increasing heart rate with or without a softening of the blood pressure. The model would predict intradialytic hypotension would eventually result if no change in ultrafiltration occurs. The model would provide a reduction in the ultrafiltration rate that would optimize ultrafiltration while circumventing hypotension.

Should the ultrafiltration rate at block 128 alternatively be determined to be within acceptable criteria limits, then the controller 70 at block 132 determines if the ultrafiltration rate can be further optimized. That is, features of the invention determine whether a faster ultrafiltration rate may be achieved without causing a harmful effect. If not, then the process will continue at block 134.

Alternatively, the ultrafiltration rate may be increased at block 136 based on the modeled results. For instance, the controller 70 may determine that the model parameters were a certain percentage under a target value/criterion. A target value may comprise a ceiling or other range of the criteria used to evaluate the ultrafiltration rate at block 128, for instance. If so, then the controller 70 may increase the ultrafiltration rate by that an amount determined by a stored algorithm or lookup table. If the hematocrit rate of change is static or at an optimisable rate, for example, substantiated by a stable blood pressure and heart rate; the mathematical model may be used to predict on increase for the ultrafiltration rate that would be optimal. The change will be made and continued monitoring will assess the ability to sustain the new fluid removal rate. Alternatively, the controller 70 may increment the ultrafiltration rate by a small, predetermined speed. In any case, the new ultrafiltration rate will be continuously evaluated as part of real time analysis. The above described processes may be fully automated, or may be augmented with manual inputs and confirmation where desired.

In practice, the system 10 removes the required amount of fluid in the shortest amount of time without causing hypotension. The system 10 estimates a patient's physiological data using an online estimation scheme, and uses the data to regulate the ultrafiltration rate blood pressure. The control system then uses the model with the data to derive an ultrafiltration rate schedule to fulfill the control system requirement. The control system uses the online data to update the ultrafiltration rate schedule as the patient's physiological conditions change.

Features of the present invention thus proactively optimize filtration rates. This contrasts prior art systems, which have been largely reactive in nature. For instance, if a sensed blood pressure was too low and a heart rate too high, a clinician would make manual adjustments. In another example prior art example, the ultrafiltration rate would be automatically blindly/unintelligently decreased over time. For instance, the ultrafiltration rate would be reduced by one-half in the first hour and then decremented according to a predetermined scheme. Such conventional schemes would not account for real time physiological fluid flux rate data. Features of the present invention use this data to intelligently adjust ultrafiltration rates. Features of the present invention use the model 94 as a comparator to address the filtration rate before the blood pressure and heart rate become problematic. The model 94 is in this manner used as a prediction tool to present expected trends and results to a clinician or controller. The filtration rate may then be adjusted automatically or manually based on the predictions.

The model 94 mitigates IDH and other problems by incorporating an automatic feedback control system that constantly evaluates the patient hemodynamic physiological conditions and appropriately adjusts the ultrafiltration rate. Features of the present invention achieve a critical balance between the ultrafiltration rate and the compensatory rate. In order to accomplish this balance, quantitative knowledge of hemodynamics are realized using the hemodynamic model 94.

The model 94 includes all significant dynamics, including blood pressure, transcapillary fluid transfer, interstitial pressure-volume relationship, lymphatic flow and a vascular stress-relaxation property. From this model, quantitative predictions are made regarding the change in blood volume and blood pressure due to hemodialysis, and this information is used to determine the optimum ultrafiltration rate. Exemplary hemodynamic and modeled parameters include arteriole resistance, venous compliance and interstitial space compliance. These parameters may change from person to person and moment to moment, and are expected to continuously change during hemodialysis. As such, the model 94 incorporates a parameter estimation feature, and takes into account pressure dynamic disregarded by the prior art.

The model 94 describes the dynamics of blood and plasma volume during ultrafiltration and incorporates the dynamics of fluid exchange through capillary wall and the dynamics of protein concentration. The dynamics of blood and plasma volume during ultrafiltration are realized by fitting the model to online blood volume changes data in order to determine the initial blood volume and filtration coefficient. The blood volume may be used to estimate the volume overload, while the filtration coefficient might be used to determine the rate at which the excess volume can be removed. With known techniques that permit analyzing the response of blood volume to ultrafiltration within a short period of time, where exponential conditions might well be controlled, it is possible to prescribe adequate ultrafiltration for subsequent treatment phases or even for the whole remaining treatment session.

A comprehensive mathematical model 94 of the hemodynamic response to hemodialysis accounts for, among other dynamics: the dynamics of sodium, urea and potassium in the intracellular and extracellular pool; fluid balance equations for the intracellular, interstitial and plasma volume; systemic and pulmonary hemodynamics (pressures); and the action of several short term arterial pressure control mechanisms. The input to the controller 70 include information coming from both arterial and cardiopulmonary pressoreceptors to accommodate systemic arterial resistance, heart rate and volume data.

In order to predict blood pressure, the model includes a set of dynamic equations used to determine model parameters for blood pressure in each compartment. One set of such dynamic algorithms and associated model parameters can be expressed as:

$$\frac{dP_{AS}}{dt} = -\frac{1}{R_S C_{AS}} P_{AS} + \frac{1}{R_S C_{AS}} P_{VS} + \frac{1}{C_{AS}} \frac{fS_L C_L A_L P_{VP}}{A_L P_{AS} + S_L K_L}$$

$$\frac{dP_{VS}}{dt} = +\frac{1}{R_S C_{VS}} P_{AS} - \frac{1}{R_S C_{VS}} P_{VS} -$$

$$\frac{1}{C_{VS}} \frac{fS_R C_R A_R P_{VS}}{A_R P_{AP} + S_R K_R} - \frac{1}{C_{VS}} Q_{ULT} + \frac{1}{C_{VS}} Q_{INF}$$

$$\frac{dP_{AP}}{dt} = -\frac{1}{R_P C_{AP}} P_{AP} + \frac{1}{R_P C_{AP}} P_{VP} + \frac{1}{C_{AP}} \frac{fS_R C_R A_R P_{VS}}{A_R P_{AP} + S_R K_R}$$

$$\frac{dP_{VP}}{dt} = +\frac{1}{R_P C_{VP}} P_{AP} - \frac{1}{R_P C_{VP}} P_{VP} - \frac{1}{C_{VP}} \frac{fS_L C_L A_L P_{VP}}{A_L P_{AS} + S_L K_L}$$

In the above pressure equations, $P_{AS}$ is the blood pressure of the systemic arterial compartment, $P_{VS}$ corresponds to the blood pressure of the systemic venous arterial compartment, $P_{AP}$ is the blood pressure of the pulmonary arterial compartment, and $P_{VP}$ is the blood pressure of the pulmonary venous compartment.

Parameters in the above model parameter equations include: systemic vascular resistance ($R_S$), the systemic arterial compartment compliance ($C_{AS}$), the systemic venous compartment compliance ($C_{VS}$), the pulmonary arterial compartment compliance ($C_{AP}$), $K_L$ and $K_R$ may be determined as a function of the compliance of the relaxed left and right ventricles, $C_L$ and $C_R$, total viscous resistance of the filling of the left and right ventricles $R_L$ and $R_R$, cardiac frequency (f), as well as the strength and compliance of the left and right ventricles $S_L$, $S_R$, $C_L$ and $C_R$, respectively. $Q_{ULT}$ is the ultrafiltration rate of fluid from the systemic venous compartment, and $Q_{INF}$ is the infusion rate of fluid into the systemic venous compartment.

To predict the blood volume and blood pressure change due to ultrafiltration, the mathematical model 94 includes the dynamic of plasma refilling, among others. Capillary, interstitial and lymphatic systems help regulate fluid volume in the circulatory circuit, which in turn, helps regulate blood pressure. Excessive fluid filters from circulatory system through capillary wall into interstitial space and hence reduces increase in blood pressure. Interstitial space fluid, returning through lymphatic system helps restore blood volume against blood loss, and therefore reduces blood pressure drop.

The below equations may be used to determine model parameters that include the fluid filtration rate from the vascular compartment to the interstitial space (e.g., the capillary filtration rate, $Q_F$), as well as systemic arterial and venous resistance ($R_{AS}$ and $R_{VS}$, respectively):

$$Q_F = \frac{(P_C - P_I) - (\Pi_P - \Pi_I)}{R_F}$$

$$R_{AS} = \frac{(P_{AS} - P_C)}{(P_{AS} - P_{VS})} R_S$$

$$R_{VS} = \frac{(P_C - P_{VS})}{(P_{AS} - P_{VS})} R_S$$

Newly introduced variables in the above equations include: the hydrostatic pressure of the fluid inside the capillary and in the interstitial space ($P_C$ and $P_I$, respectively), the plasma colloid osmotic pressure of the fluid in the interstitial space and inside the capillary ($\Pi_I$ and $\Pi_P$, respectively), and the reciprocal of the filtration coefficient of the capillary membrane ($R_F$).

The below equation may be used to determine a model parameter that includes the hydrostatic pressure of the fluid in the interstitial space ($P_I$). The equation includes the lymph flow rate ($Q_{LYMPH}$) as a variable.

$$\frac{dP_I}{dt} = \frac{(P_C - P_I) - (\Pi_P - \Pi_I)}{R_F C_I} - \frac{1}{C_I} Q_{LYMPH}$$

The below dynamic equations may be additionally or alternatively used to determine model parameters that include the respective blood pressures in the pulmonary arterial and venous compartments ($P_{AP}$ and $P_{VP}$) the systemic and venous arterial compartments ($P_{AS}$ and $P_{VS}$), as well as the hydrostatic pressure of the fluid in the interstitial space ($P_I$):

$$\frac{dP_{AP}}{dt} = -\frac{1}{R_P C_{AP}} P_{AP} + \frac{1}{R_P C_{AP}} P_{VP} + \frac{1}{C_{AP}} \frac{fS_R C_R A_R P_{VS}}{A_R P_{AP} + S_R K_R}$$

$$\frac{dP_{VP}}{dt} = \frac{1}{R_P C_{VP}} P_{AP} - \frac{1}{R_P C_{VP}} P_{VP} - \frac{1}{C_{VP}} \frac{fS_L C_L A_L P_{VP}}{A_L P_{AS} + S_L K_L}$$

$$\frac{dP_{AS}}{dt} =$$
$$-\frac{1}{R_{AS}}\left(1 - \frac{R}{R_{AS}}\right)\frac{1}{C_{AS}} P_{AS} + \frac{1}{R_{AS}} \frac{R}{R_{VS}} \frac{1}{C_{AS}} P_{VS} + \frac{1}{R_{AS}} \frac{R}{R_F} \frac{1}{C_{AS}} P_I +$$
$$\frac{1}{R_{AS}} \frac{R}{R_F} \frac{1}{C_{AS}} \Pi_P - \frac{1}{R_{AS}} \frac{R}{R_F} \frac{1}{C_{AS}} \Pi_I + \frac{1}{C_{AS}} \frac{fS_L C_L A_L P_{VP}}{A_L P_{AS} + S_L K_L}$$

$$\frac{dP_{VS}}{dt} = \frac{1}{R_{VS}} \frac{R}{R_{AS}} \frac{1}{C_{VS}} P_{AS} - \frac{1}{R_{VS}}\left(1 - \frac{R}{R_{VS}}\right)\frac{1}{C_{VS}} P_{VS} +$$
$$\frac{1}{R_{VS}} \frac{R}{R_F} \frac{1}{C_{VS}} P_I + \frac{1}{R_{VS}} \frac{R}{R_F} \frac{1}{C_{VS}} \Pi_P - \frac{1}{R_{VS}} \frac{R}{R_F} \frac{1}{C_{VS}} \Pi_I +$$
$$\frac{1}{C_{VS}} Q_{LYMPH}(P_I) - \frac{1}{C_{VS}} \frac{fS_R C_R A_R P_{VS}}{A_R P_{AP} + S_R K_R} - \frac{1}{C_{VS}} Q_{ULT} + \frac{1}{C_{VS}} Q_{INF}$$

$$\frac{dP_I}{dt} = \frac{1}{R_{AS}} \frac{R}{R_F} \frac{1}{C_I} P_{AS} + \frac{1}{R_{VS}} \frac{R}{R_F} \frac{1}{C_I} P_{VS} - \frac{1}{R_F}\left(1 - \frac{R}{R_F}\right)\frac{1}{C_I} P_I -$$
$$\frac{1}{R_F}\left(1 - \frac{R}{R_F}\right)\frac{1}{C_I} \Pi_P + \frac{1}{R_F}\left(1 - \frac{R}{R_F}\right)\frac{1}{C_I} \Pi_I - \frac{1}{C_I} Q_{LYMPH}(P_I)$$

$$\frac{dP_{VS}}{dt} = \left(\frac{k_{S_1}}{A^2} + \frac{k_{S_2}}{A^2}\right)\frac{1}{R_{VS}} \frac{R}{R_{AS}} P_{AS} -$$
$$\left(\frac{k_{S_1}}{A^2} \frac{A^2}{\mu_{DI}} + \left(\frac{k_{S_1}}{A^2} + \frac{k_{S_2}}{A^2}\right)\frac{1}{R_{VS}}\left(1 - \frac{R}{R_{VS}}\right)\right) P_{VS} + \left(\frac{k_{S_1}}{A^2} + \frac{k_{S_2}}{A^2}\right)\frac{1}{R_{VS}} \frac{R}{R_F} P_I +$$

-continued $$\left(\frac{k_{S_1}}{A2} + \frac{k_{S_2}}{A2}\right)\frac{1}{R_{VS}}\frac{R}{R_F}\Pi_P - \left(\frac{k_{S_1}}{A2} + \frac{k_{S_2}}{A2}\right)\frac{1}{R_{VS}}\frac{R}{R_F}\Pi_I +$$
$$\left(\frac{k_{S_1}}{A2} + \frac{k_{S_2}}{A2}\right)Q_{LYMPH}(P_I) - \left(\frac{k_{S_1}}{A2} + \frac{k_{S_2}}{A2}\right)\frac{fS_R C_R A_R P_{VS}}{A_R P_{AP} + S_R K_R} +$$
$$\left(\frac{k_{S_1}}{A2} + \frac{k_{S_2}}{A2}\right)Q_{INF} - \left(\frac{k_{S_1}}{A2} + \frac{k_{S_2}}{A2}\right)Q_{ULT} + \frac{k_{S_1}}{A2} + \frac{k_{S_2}}{aS}\frac{A^2}{\mu_{D_1}}V_{VS}$$

The hemodynamic model 94 of another or the same embodiment may include stress-relaxation properties and factors and equations to determine the pulmonary arterial and venous compartments ($P_{AP}$ and $P_{VP}$), the systemic and venous arterial compartments ($P_{AS}$ and $P_{VS}$) the hydrostatic pressure of the fluid in the interstitial space ($P_I$), as well as the volume in the systemic venous compartment ($V_{VS}$).

$$\frac{dP_{AS}}{dt} = -\frac{1}{R_{AS}}\left(1 - \frac{R}{R_{AS}}\right)\frac{1}{C_{AS}}P_{AS} + \frac{1}{R_{AS}}\frac{R}{R_{VS}}\frac{1}{C_{AS}}P_{VS} + \frac{1}{R_{AS}}\frac{R}{R_F}\frac{1}{C_{AS}}P_I +$$
$$\frac{1}{R_{AS}}\frac{R}{R_F}\frac{1}{C_{AS}}\Pi_P - \frac{1}{R_{AS}}\frac{R}{R_F}\frac{1}{C_{AS}}\Pi_I + \frac{1}{C_{AS}}\frac{fS_L C_L A_L P_{VP}}{A_L P_{AS} + S_L K_L}$$

$$\frac{dP_{AP}}{dt} = -\frac{1}{R_P C_{AP}}P_{AP} + \frac{1}{R_P C_{AP}}P_{VP} + \frac{1}{C_{AP}}\frac{fS_R C_R A_R P_{VS}}{C_{AP} A_R P_{AP} + S_R K_R}$$

$$\frac{dP_{VP}}{dt} = \frac{1}{R_P C_{VP}}P_{AP} - \frac{1}{R_P C_{VP}}P_{VP} - \frac{1}{C_{VP}}\frac{fS_L C_L A_L P_{VP}}{A_L P_{AS} + S_L K_L}$$

$$\frac{dP_I}{dt} = \frac{1}{R_{AS}}\frac{R}{R_F}\frac{1}{C_I}P_{AS} + \frac{1}{R_{VS}}\frac{R}{R_F}\frac{1}{C_I}P_{VS} - \frac{1}{R_F}\left(1 - \frac{R}{R_F}\right)\frac{1}{C_I}P_I -$$
$$\frac{1}{R_F}\left(1 - \frac{R}{R_F}\right)\frac{1}{C_I}\Pi_P + \frac{1}{R_F}\left(1 - \frac{R}{R_F}\right)\frac{1}{C_I}\Pi_I - Q_{LYMPH}(P_I)$$

$$\frac{dP_{VS}}{dt} = \frac{1}{R_{VS}}\frac{R}{R_{AS}}P_{AS} - \frac{1}{R_{VS}}\left(1 - \frac{R}{R_{VS}}\right)P_{VS} + \frac{1}{R_{VS}}\frac{R}{R_F}P_I + \frac{1}{R_{VS}}\frac{R}{R_F}\Pi_P -$$
$$\frac{1}{R_{VS}}\frac{R}{R_F}\Pi_I + Q_{LYMPH}(P_I) - \frac{fS_R C_R A_R P_{VS}}{A_R P_{AP} + S_R K_R} + Q_{INF} - Q_{ULT}$$

Figure 5:
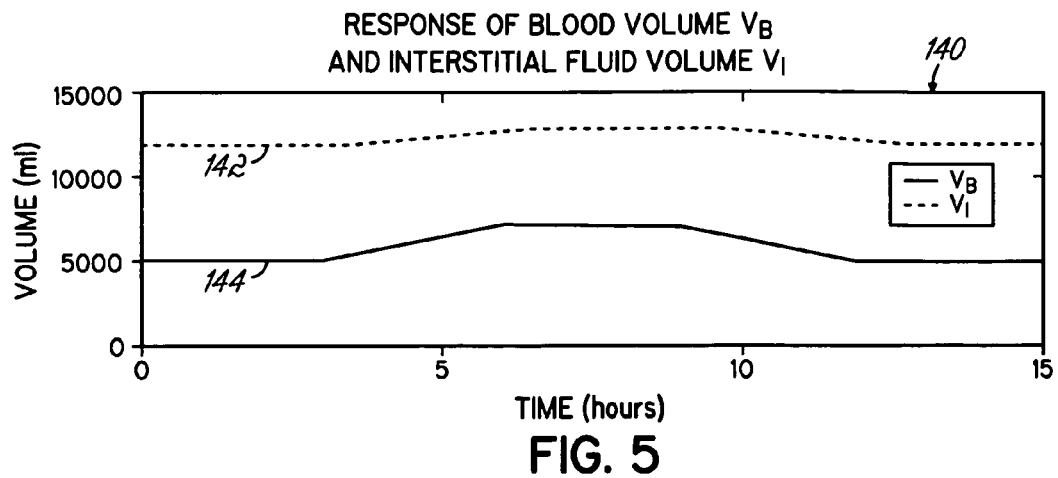
FIG. 5 is a graphical representation of blood and interstitial fluid volume response parameters modeled by the controller of FIG. 2.
Figure 6:
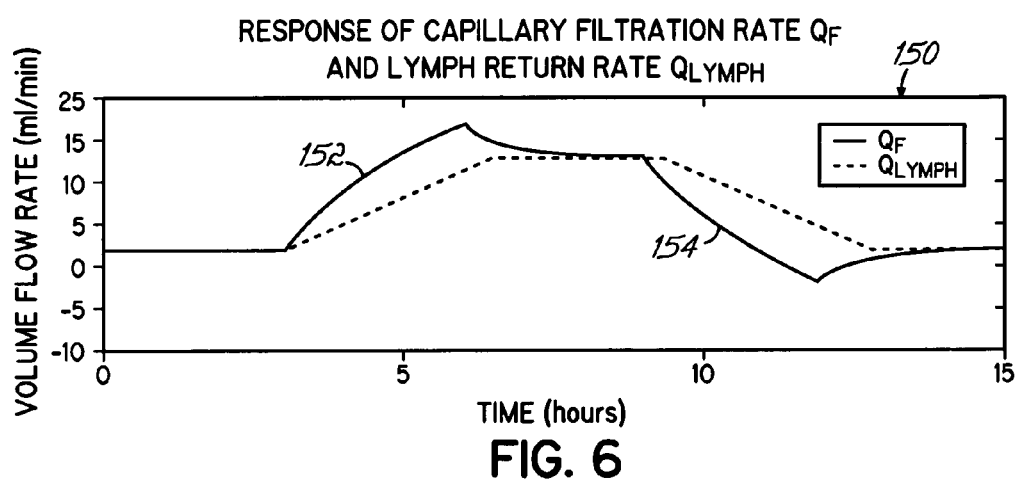
FIG. 6 is a graphical representation of capillary filtration and lymph return rate parameters modeled by the controller of FIG. 2.

As will be appreciated by one of skill in the art, any of the algorithms used by the system 10 can be represented graphically, as well as in the above listed mathematical format. Furthermore, mathematical equations may be approximated in a discrete-time format. FIGS. 5 and 6 graphically show parameters predicted by the modeling processes of the controller of FIG. 2. These parameters include the capillary filtration rate, $Q_F$, the lymph return rate, $Q_{LYMPH}$, and the plasma return rate, $Q_{PR}=Q_{LYMPH}-Q_F$.

Turning more particularly to FIG. 5, the graph 140 shows the ability of the model 94 to predict the distribution of the fluid between the vascular compartment, $V_b$ (denoted by solid line 144), and the interstitial fluid compartment, $V_I$ (shown as dashed line 142). During infusion, the controller 70 uses the model to predict a rise in both $V_b$ and $V_I$. When the infusion stops, $V_b$ falls slightly before settling down to a new equilibrium. The rise in $V_I$ also stops and settles to a new equilibrium, but without falling. During ultrafiltration, both $V_b$ and $V_I$ fall. When the ultrafiltration stops, $V_b$ rises slightly, then settles up to the equilibrium point before infusion. The fall in $V_I$ also stops and settles to the equilibrium before infusion, but without rising.

FIG. 6 shows a graphical representation 150 of capillary filtration and lymph return rate parameters ($Q_F$ and $Q_{LYMPH}$) modeled by the controller 70. During the infusion, the model 94 predicts a rise in both $Q_F$ and $Q_{LYMPH}$, with $Q_F$ rising faster than $Q_{LYMPH}$. When the infusion stops, $Q_F$ (shown as solid line 152) decays slightly, then settles to a new equilibrium. $Q_{LYMPH}$ (shown as dashed line 154) slows down in rising and settles at a new equilibrium, which is the same as the equilibrium point of $Q_F$. During ultrafiltration, the model predicts a fall in both $Q_F$ and $Q_{LYMPH}$. $Q_F$ falls faster than $Q_{LYMPH}$ and eventually goes negative towards the end of the ultrafiltration period. When ultrafiltration stops, $Q_F$ rises slightly, then settles to an equilibrium point before infusion. $Q_{LYMPH}$ slows down in falling and settles at the equilibrium point before infusion, which is the same as the equilibrium point of $Q_F$.

Figure 7:
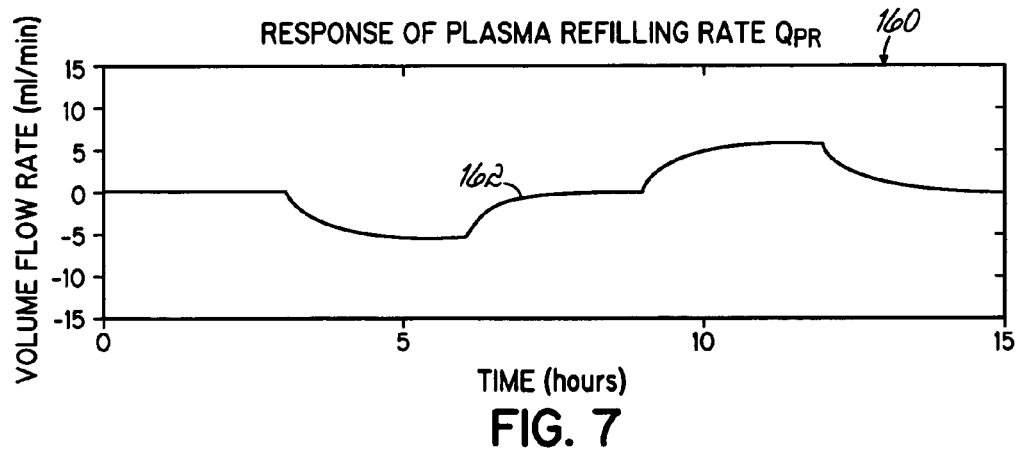
FIG. 7 is a graphical representation of the response of the plasma refilling rate parameter modeled by the controller of FIG. 2.

FIG. 7 is a graphical representation 160 of the response of the plasma refilling rate parameter modeled by the controller 70. Nephrologists use the term "plasma refilling rate," to refer to the mechanism of the restoration of the blood volume during an ultrafiltration procedure. Because the plasma return rate $Q_{PR}$ is equal to $Q_{LYMPH}-Q_F$, during infusion, the model predicts a fall in $Q_{PR}$ (charted as line 162) with a decreasing rate of falling with infusion time. When the infusion stops, $Q_{PR}$ gradually rises to an equilibrium point of zero. During the ultrafiltration, the model predicts a rise in $Q_{pr}$, with a decreasing rate of rising with ultrafiltration time. When the ultrafiltration stops, $Q_{PR}$ gradually falls down to the equilibrium point of zero again, which is the same as the equilibrium point before infusion.

While the present invention has been illustrated by a description of various preferred embodiments and while these embodiments have been described in considerable detail in order to describe the best mode of practicing the invention, it is not the intention of applicant to restrict or in any way limit the scope of the appended claims to such detail. For instance, while the embodiments described above focus mainly on ultrafiltration processes, one skilled in the art will recognize that features of the present invention may have equal application in other areas of extracorporeal renal replacement and hemofiltration, to include hemodialysis, hemofiltration, hemodiafiltration and plasmapheresis processes. As used herein, the term "infusate" is defined to include dialysate fluid or any other replacement fluids which may be supplied to the patient as a part of the extracorporeal renal replacement procedures.

Additional advantages and modifications within the spirit and scope of the invention will readily appear to those skilled in the art. For example, the model and criteria of an embodiment may include actual clinical data, as opposed or in addition to algorithms. Such data may be downloaded from a clinical source. Furthermore the equations included herein are not meant as an exhaustive list of all equations comprising a model. One skilled in the art will appreciate that many additional known algorithms may be used to supplant or augment those equations included in the specification. In any case, the invention itself should only be defined by the appended claims, wherein We claim:

We claim:

1. An extracorporeal renal replacement system for fluid removal from the blood of a patient, comprising:
   a pump capable of pumping a liquid selected from the group consisting of infusate, drained fluid, and blood in the extracorporeal renal replacement system;
   a flow rate sensor for measuring the flow rate of fluid in the system generated by the pump, the flow rate sensor providing flow rate data signals correlated to the fluid flow rate;
   a patient sensor for measuring a physiological condition of the patient, the patient sensor providing patient sensor data signals correlated to the physiological condition; and
   a controller in communication with the pump, the flow rate sensor and the patient sensor, the controller configured to receive the flow rate data signals and the patient sensor data signals and analyze the flow rate data signals and the patient parameter data signals using a mathematical model to predict a direction of an ultrafiltration rate based on current conditions, and then to automatically initiate generation of a corrective output signal for the pump to adjust the flow rate of liquid generated by the pump for regulating fluid removal from the patient's blood.

2. The extracorporeal renal replacement system of claim 1, wherein the controller is further configured to initiate generation of the output signal by using the model to process the flow rate data and the physiological condition to determine a model parameter, and to adjust the flow rate if the model parameter fails to conform with stored criteria.

3. The extracorporeal renal replacement system of claim 2, wherein the model parameter is selected from the group consisting of at least one of: blood pressure data, transcapillary fluid transfer data, interstitial pressure data, interstitial volume data, interstitial pressure-volume relationship data, lymphatic flow data, arteriole resistance data, mixed venous oxygen compliance data, venous compliance data, interstitial space compliance data, sodium data, urea data, protein data, potassium data in an intracellular and extracellular pool, fluid balance data, systemic hemodynamic data, pulmonary hemodynamic data, arterial pressure control mechanism data, arterial and cardiopulmonary pressoreceptor data, volume data, blood pressure data of a systemic arterial compartment, blood pressure data of a systemic venous compartment, blood pressure data of a pulmonary arterial compartment, blood pressure data of a pulmonary venous compartment, hydrostatic pressure data of a fluid inside a capillary, pulmonary arterial and venous compartment data, systemic arterial compartment data, venous arterial compartment data, hydrostatic pressure data of a fluid in interstitial space, volume data in a systemic venous compartment, systemic arterial and venous resistance data, distribution data relating to fluid between a vascular compartment and an interstitial fluid compartment, capillary filtration data, lymph return rate data and plasma refilling rate data.

4. The extracorporeal renal replacement system of claim 1, wherein the controller is further configured to continuously adjust the flow rate of the liquid.

5. The extracorporeal renal replacement system of claim 1, wherein the physiological condition is selected from the group consisting of at least one of: heart rate data, blood pressure data, plasma return rate data, systemic arterial pressure data, pulse pressure data, pulse rate data, estimated cardiac ejection time data, estimated stroke volume data, estimated stroke volume index data, estimated cardiac output data, estimated cardiac index data, large artery elasticity index data, small artery elasticity index data, systemic vascular resistance data and total vascular impedance data.

6. The extracorporeal renal replacement system of claim 1, wherein the flow rate comprises an ultrafiltration rate.

7. The extracorporeal renal replacement system of claim 1, wherein the patient sensor is selected from the group consisting of at least one of: a blood pressure monitor providing blood pressure data signals, and a heart rate monitor providing heart rate data signals.

8. The extracorporeal renal replacement system of claim 1, wherein the mathematical model comprises a series of equations configured to assess the flow rate data signals and the patient parameter data signals in terms of the ultrafiltration rate.

9. The extracorporeal renal replacement system of claim 1, wherein the mathematical model includes a set of variables and a set of quantitative relationships between the set of variables.

10. The extracorporeal renal replacement system of claim 1, wherein the mathematical model includes a series of mathematical equations descriptive of hemodynamic parameters.

* * * * *

UNITED STATES PATENT AND TRADEMARK OFFICE
CERTIFICATE OF CORRECTION

PATENT NO. : 7,785,463 B2
APPLICATION NO. : 11/378051
DATED : August 31, 2010
INVENTOR(S) : John J. Bissler It is certified that error appears in the above-identified patent and that said Letters Patent is hereby corrected as shown below:

Title Page; item (56);
On Page 2 under Other Publications, in the first line of the second column, change "Demodialysis" to --Hemodialysis--.

In column 2:
Line 24, change "bodies" to --body's--
Line 51, change "Patient sensor," to --A patient sensor--
Line 56, after "generation", insert --of--.

In column 5, line 9, change "maybe" to --may be--.

In column 8:
Line 46, change "repeats" to --repeat--
Line 60, after "blood pressure", delete "heart rate".

In column 9:
Line 30, after "rate", delete "excess line and"
Line 59, after "by", delete "that"
Line 63, change "on" to --an--.

In column 10:
Line 19, after "another", delete "example"
Line 41, change "are" to --is--.

In column 11, line 12, change "include" to --includes--.

In column 12, line 35, before "the", insert --,--.

In column 13, line 15, before "the", insert --,--.

In column 14, line 28, change "applicant" to --applicants--.

Signed and Sealed this

Twenty-third Day of November, 2010

David J. Kappos
*Director of the United States Patent and Trademark Office*